United States Patent
Moreira Araujo et al.

(10) Patent No.: US 10,161,908 B2
(45) Date of Patent: Dec. 25, 2018

(54) APPARATUS FOR DETERMINING A CHARACTERISTIC OF A FLUID HAVING A DEVICE CONFIGURED TO MEASURE A HYDRODYNAMIC PRESSURE OF THE FLUID

(71) Applicant: Infineon Technologies AG, Neubiberg (DE)

(72) Inventors: Rui Miguel Moreira Araujo, Munich (DE); Bernd Goller, Otterfing (DE); Dominic Maier, Pleystein (DE)

(73) Assignee: INFINEON TECHNOLOGIES AG, Neubiberg (DE)

( * ) Notice: Subject to any disclaimer, the term of this patent is extended or adjusted under 35 U.S.C. 154(b) by 283 days.

(21) Appl. No.: 15/079,889

(22) Filed: Mar. 24, 2016

(65) Prior Publication Data

US 2017/0276646 A1    Sep. 28, 2017

(51) Int. Cl.
*G01N 29/024*    (2006.01)
*G01N 29/02*    (2006.01)
*H04R 1/02*    (2006.01)
*G01N 29/14*    (2006.01)
(Continued)

(52) U.S. Cl.
CPC ......... *G01N 29/024* (2013.01); *G01N 29/022* (2013.01); *G01N 29/14* (2013.01); *G01N 29/42* (2013.01); *H04R 1/028* (2013.01); *G01N 2291/02809* (2013.01); *H01L 2224/48091* (2013.01); *H01L 2224/73265* (2013.01); *H01L 2924/10155* (2013.01);
(Continued)

(58) Field of Classification Search
CPC ...... G01N 29/024; G01N 29/42; G01N 29/14; G01N 29/022; G01N 2291/02809; H04R 1/028; H04R 2499/11; H04R 1/04; H04R 2201/003; H01L 2924/16152; H01L 2224/73265; H01L 2924/10155; H01L 2224/48091
See application file for complete search history.

(56) References Cited

U.S. PATENT DOCUMENTS 6,097,121 A * 8/2000 Oku .................. G11B 19/2009
                                                        310/425
6,447,167 B1 * 9/2002 Kashiwada .......... F16C 17/107
                                                        384/100
(Continued)

FOREIGN PATENT DOCUMENTS

KR    20140028126 A    3/2014
KR    20150113915 A    10/2015

*Primary Examiner* — Bilkis Jahan
(74) *Attorney, Agent, or Firm* — Slater Matsil, LLP

(57) ABSTRACT

Embodiments of the present disclosure provide an apparatus for determining a characteristic of a fluid. The apparatus may include a device configured to determine a hydrodynamic pressure of the fluid. The apparatus may further include a sensor configured to determine a hydrostatic pressure of the fluid or at least one component of the fluid. The apparatus may also include a common substrate on which the sensor and the device configured to determine a hydrodynamic pressure of the fluid may be commonly arranged, and an ASIC (Application Specific Integrated Circuit) which may be electrically coupled with at least one of the device or the sensor. The ASIC may be at least partially embedded in the common substrate.

20 Claims, 11 Drawing Sheets

(51) Int. Cl.
*G01N 29/42* (2006.01)
*H04R 1/04* (2006.01)

(52) U.S. Cl.
CPC ...... *H01L 2924/16152* (2013.01); *H04R 1/04* (2013.01); *H04R 2201/003* (2013.01); *H04R 2499/11* (2013.01)

(56) References Cited

U.S. PATENT DOCUMENTS

| | | | |
|---|---|---|---|
| 7,819,585 B2 * | 10/2010 | Satoji | A61K 38/4893 |
| | | | 384/100 |
| 2009/0208153 A1 * | 8/2009 | Yamashita | B21J 5/02 |
| | | | 384/107 |
| 2012/0087521 A1 | 4/2012 | Delaus et al. | |
| 2013/0162080 A1 * | 6/2013 | Yu | H02K 5/1675 |
| | | | 310/90 |
| 2014/0205467 A1 * | 7/2014 | Yanai | F04B 35/04 |
| | | | 417/53 |
| 2014/0264654 A1 | 9/2014 | Salmon | |
| 2014/0295420 A1 * | 10/2014 | Ovsyanko | B03C 1/01 |
| | | | 435/6.11 |
| 2015/0010415 A1 * | 1/2015 | Yamada | F04D 13/064 |
| | | | 417/420 |
| 2015/0276529 A1 | 10/2015 | Wiesbauer et al. | |
| 2015/0321906 A1 | 11/2015 | Tsai et al. | |

* cited by examiner

APPARATUS FOR DETERMINING A CHARACTERISTIC OF A FLUID HAVING A DEVICE CONFIGURED TO MEASURE A HYDRODYNAMIC PRESSURE OF THE FLUID

TECHNICAL FIELD

This disclosure relates in general to the determination of a characteristic of a fluid, and, in particular embodiments, to a device for determining a characteristic of a fluid.

BACKGROUND

Fluids may comprise both liquid and gas phases of matter and may include, for instance, liquids, gases, plasmas and plastic solids. Fluids may comprise one or more characteristics, such as temperature, an individual composition, a concentration of one or more components, a certain kind of fluid, or an amount of pressure, for example. In particular pressure may further be divided into hydrostatic pressure and hydrodynamic pressure. Apparatuses and devices may be used for determining one or more of such characteristics of a fluid.

SUMMARY

Embodiments provide an apparatus for determining a characteristic of a fluid. The apparatus may comprise a device to determine a hydrodynamic pressure of the fluid and a sensor to determine a hydrostatic pressure of the fluid or at least one component of the fluid. The apparatus may further comprise a common substrate on which the sensor and the device to determine a hydrodynamic pressure of the fluid are arranged. Furthermore, the apparatus may comprise an ASIC (Application Specific Integrated Circuit) which may be electrically coupled with at least one of the sensor and the device to determine a hydrodynamic pressure of the fluid. The ASIC may be at least partly embedded in the common substrate.

Further embodiments provide a device for determining a characteristic of a fluid, the device may comprise a sensor being arranged on a substrate, and an ASIC which may be electrically coupled with the sensor. The ASIC may further be at least partially embedded in the substrate. The sensor is configured to determine a hydrostatic pressure of the fluid or at least one component of the fluid.

Further embodiments provide communication device that may comprise a microphone and a sensor to determine a hydrostatic pressure of a fluid or at least one component of the fluid. The communication device may further comprise a common substrate on which the microphone and the sensor are arranged, and an ASIC (Application Specific Integrated Circuit) which may be electrically coupled with at least one of the microphone or the sensor. Furthermore, the communication device may comprise a fluid port that provides a fluidic connection between an inside and an outside of the communication device. The ASIC may be at least partly embedded in the common substrate.

BRIEF DESCRIPTION OF THE DRAWINGS

Embodiments of the present disclosure are described herein making reference to the appended drawings, wherein.

DETAILED DESCRIPTION OF ILLUSTRATIVE EMBODIMENTS

Figure 1:
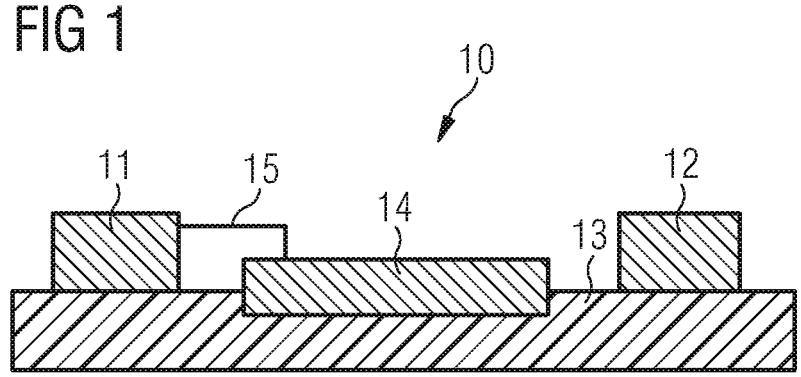
FIG. 1 shows a schematic cross-sectional view of an apparatus for determining a characteristic of a fluid according to an example.

Equal or equivalent elements or elements with equal or equivalent functionality are denoted in the following description by equal or equivalent reference numerals.

In the following description, a plurality of details is set forth to provide a more thorough explanation of embodiments of the present disclosure. However, it will be apparent to those skilled in the art that embodiments of the present disclosure may be practiced without these specific details. In other instances, well known structures and devices are shown in block diagram form rather than in detail in order to avoid obscuring embodiments of the present disclosure. In addition, features of the different embodiments described hereinafter may be combined with each other, unless specifically noted otherwise.

Fluids may comprise both liquid and gas phases of matter and may include, for instance, liquids, gases, plasmas and plastic solids. Fluids may comprise one or more characteristics, such as temperature, an individual composition, a concentration of one or more components, a certain kind of fluid, or an amount of pressure, for example. In particular pressure may further be divided into hydrostatic pressure and hydrodynamic pressure. Apparatuses and devices according the present disclosure may be used for determining one or more of such characteristics of a fluid.

The hydrostatic pressure, sometimes also referred to as open pressure or gravitational pressure, is the pressure in a static fluid, i.e. in a fluid that is substantially at rest. The hydrostatic pressure may ensue due to gravitation. For example, the atmospheric pressure may be a hydrostatic pressure. Even though the atmospheric pressure may vary over time, the variation is so slow that it can be assumed to be static. Thus, the hydrodynamic pressure may characterize fluids substantially at rest.

The hydrodynamic pressure, sometimes also referred to as dynamic pressure or velocity pressure, results from the kinetic energy of a streaming fluid at the surface of a body inside this stream. The hydrodynamic pressure may vary faster than the hydrostatic pressure does, and the variation of the hydrodynamic pressure may correspond with the variation in velocity of the streaming fluid. Thus, the hydrodynamic pressure may characterize moving fluids.

FIG. 1 shows an example of an apparatus 10 for determining a characteristic of a fluid according to the present disclosure. The apparatus 10 comprises a device 11 to determine a hydrodynamic pressure of a fluid.

The apparatus 10 further comprises a sensor 12. The sensor 12 may be configured to determine a hydrostatic pressure of the fluid. The sensor 12 may further be configured to determine one or more components of the fluid.

The apparatus 10 further comprises a common substrate 13 on which the sensor 12 and the device 11 configured to determine a hydrodynamic pressure of the fluid are commonly arranged.

The apparatus 10 further comprises an ASIC 14 (Application Specific Integrated Circuit). The ASIC 14 may be electrically coupled with the device 11 configured to determine a hydrodynamic pressure of the fluid, for example, by means of an electrical conductor 15. The electrical conductor 15 may be routed inside the ASIC. Additionally or alternatively, the ASIC 14 may be electrically coupled with the sensor 12.

As can be seen in FIG. 1, the ASIC 14 is at least partly embedded in the common substrate 13.

Figure 2:
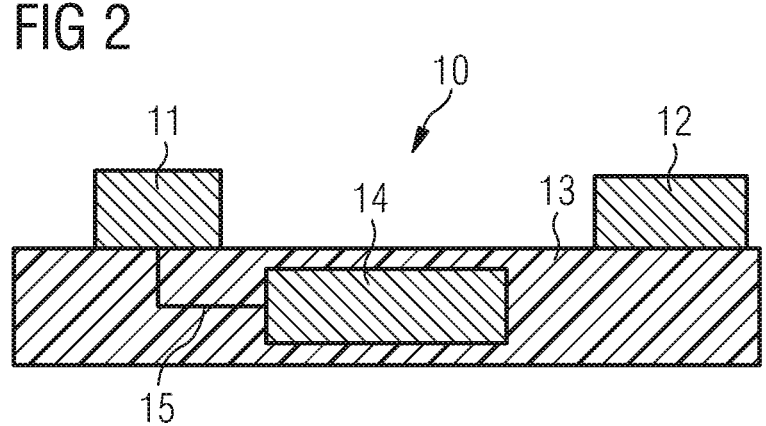
FIG. 2 shows a further schematic cross-sectional view of an apparatus for determining a characteristic of a fluid according to an example.

FIG. 2 shows a further example of an apparatus 10 according to the present disclosure. In this example, the ASIC 14 is entirely embedded in the common substrate 13. The ASIC 14 may be electrically coupled with the device 11 configured to determine a hydrodynamic pressure of the fluid, for example, by means of an electrical conductor 15. The electrical conductor 15 may be routed inside the ASIC, as shown in FIG. 2, or outside the ASIC 14 as shown in FIG. 1. Additionally or alternatively, the ASIC 14 may be electrically coupled with the sensor 12.

Figure 3:
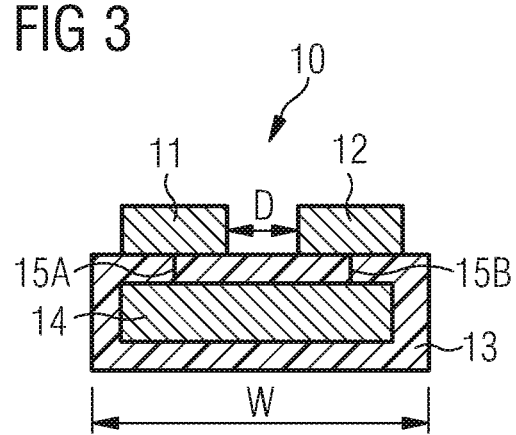
FIG. 3 shows a further schematic cross-sectional view of an apparatus for determining a characteristic of a fluid according to an example.

FIG. 3 shows a further example of an apparatus 10 according to the present disclosure. The apparatus 10 comprises an ASIC 14 that is entirely embedded in the common substrate 13. Embedding the ASIC 14 in the common substrate 13 may allow to the relative lateral distance 'D' between the sensor 12 and the device 11 configured to determine a hydrodynamic pressure of the fluid, for example compared to the examples previously discussed with reference to FIG. 1 and FIG. 2.

The arrangement shown in FIG. 3 may also allow to reduce the total width 'W' of the apparatus 10. Furthermore, it may allow to reduce the length of the electrical conductors 15A, 15B to electrically couple the sensor 12 or the device 11 configured to determine a hydrodynamic pressure of the fluid with the ASIC 14.

According to an example, the device 11 configured to determine a hydrodynamic pressure of the fluid may be at least one of a mechanical device, an electrical device and an electromechanical device.

According to an example, the device 11 configured to determine a hydrodynamic pressure of the fluid may be a microphone. A microphone 11 may be configured to determine an acoustic pressure, or sound pressure, as an example for a hydrodynamic pressure.

The sensor 12 is configured to determine a hydrostatic pressure instead. According to an example, the sensor 12 is a pressure sensor. The sensor 12 may, for instance, be an air pressure sensor for measuring ambient air pressure. Thus, the sensor 12 may be used for barometric measurements. The sensor 12 may also be configured to measure slow variations of air pressure, which may ensue, for example, due to variations of height, such as during diving, flying or climbing activities.

As mentioned before, the device 11 configured to determine a hydrodynamic pressure of the fluid may be a microphone which may be reactive to fast variations in the fluid pressure, while the sensor 12 may be reactive to slow variations in the fluid pressure. The device 11 and the sensor 12 may be configured to generate electrical signals in response to pressure variations of the fluid.

Figure 4:
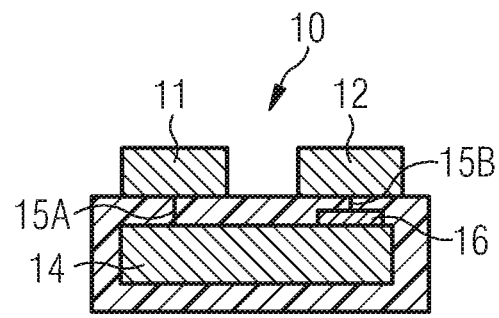
FIG. 4 shows a further schematic cross-sectional view of an apparatus for determining a characteristic of a fluid according to an example.

As can be seen in FIG. 4, the apparatus 10 may comprise a low-pass filter 16 or a bandpass-filter 16 configured to attenuate electrical signals from the sensor 12 which electrical signals are generated in response to pressure variations with a frequency of more than 20 Hz or with a frequency of more than 10 Hz. In other words, the filter element 16 may be configured, according to an example, to let frequencies pass which lay below 20 Hz. In a further example, the filter element 16 may be configured to let frequencies pass which lay below 10 Hz.

According to some further examples, the filter element 16 may be configured to let frequencies pass which lay below 5 Hz, or which lay below 1 Hz. Signals with a higher frequency may be attenuated.

Accordingly, the sensor 12 is reactive to slow variations in the fluid pressure which variations comprise a frequency of less than 20 times per second, or less than 10 times per second. Thus, the corresponding fluid pressure may be regarded as a hydrostatic fluid pressure.

In an example, pressure variations with frequencies above 10 Hz may be regarded as fast pressure variations. In a further example, pressure variations with frequencies above 20 Hz may be regarded as fast pressure variations. Thus, the corresponding fluid pressure may be regarded as a hydrodynamic fluid pressure. An example of a hydrodynamic fluid pressure is a sound pressure.

Accordingly, the device 11 is configured to determine such a hydrodynamic pressure of the fluid. Accordingly, the device 11 may be reactive to fast pressure variations while the sensor 12 may be reactive to slow pressure variations.

As mentioned above, the sensor 12 may be configured to determine a hydrostatic pressure. The sensor 12 may, however, also be configured to determine at least one component of the fluid.

In an example, the sensor 12 may be a gas sensor configured to determine the concentration of the at least one component of the fluid. Additionally or alternatively, the sensor 12 may be a gas sensor configured to determine the composition of the fluid. Further additionally or alternatively, the sensor 12 may be a gas sensor configured to determine the type of the fluid. Thus, the gas sensor 12 may determine a characteristic of a fluid preferably in its gaseous phase.

A fluid in a gaseous phase may comprise one or more components. As an example, dry ambient air may comprise 78.09% nitrogen, 20.95% oxygen, 0.93% argon, 0.039% carbon dioxide, and small amounts of other gases. Dry ambient air may also comprise a variable amount of water vapor, for example between about 1% at sea level, and about 0.4% over the entire atmosphere.

The gas sensor 12 may be configured to detect or determine at least one component of the fluid, i.e. to identify the respective component, for example, nitrogen, oxygen or the like.

The gas sensor 12 may be configured to determine the concentration of the at least one component of the fluid, i.e. to detect or determine the amount or percentage of the at least one component contained in the fluid.

The gas sensor 12 may be configured to determine the composition of the fluid, i.e. to detect or determine one or more or maybe even all of the components contained in the fluid. The gas sensor 12 may be configured to determine a quantitative composition of the fluid, i.e. to detect or determine the type of a component or components contained in the fluid. The gas sensor 12 may also be configured to determine a qualitative composition of the fluid, i.e. to detect or determine the amount of a component or components contained in the fluid.

The gas sensor 12 may also be configured to detect or determine the type of the fluid, for example to determine that the fluid is dry ambient air.

According to an example, the sensor 12 may be a MEMS, i.e. a Micro-Electro-Mechanical-System. Additionally or alternatively, the device 11 configured to determine a hydrodynamic pressure of the fluid may be a MEMS. A MEMS may comprise a small form factor which may reduce the form factor or package size of the apparatus of the present disclosure.

Figure 5:
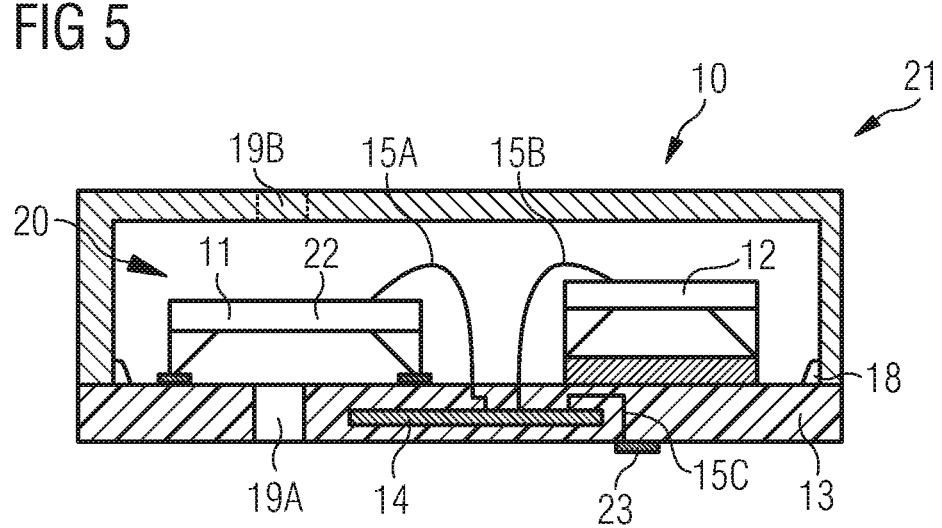
FIG. 5 shows a schematic side view of an apparatus for determining a characteristic of a fluid according to an example.

FIG. 5 shows an example of an apparatus 10 for determining a characteristic of a fluid in accordance with the present disclosure. The apparatus 10 comprises a device 11 configured to determine a hydrodynamic pressure of the fluid.

The apparatus 10 further comprises a sensor 12 configured to determine a hydrostatic pressure of the fluid or at least one component of the fluid.

The apparatus 10 further comprises a common substrate 13 on which the sensor 12 and the device 11 configured to determine a hydrodynamic pressure of the fluid are commonly arranged.

The apparatus 10 further comprises an ASIC 14 which is embedded in the common substrate 13. The ASIC 14 is electrically coupled by means of electrical conductors 15A, 15B, with the sensor 12 and the device 11 configured to determine a hydrodynamic pressure of the fluid.

The apparatus 10 according to this example, further comprises a cover 17. The cover 17 is mechanically coupled with the common substrate 13. The cover 17 may surround the sensor 12 and the device 11 configured to determine a hydrodynamic pressure of the fluid. In other words, the cover 17 may provide a lid or a housing for covering or housing at least one of the sensor 12 and the device 11 configured to determine a hydrodynamic pressure of the fluid.

The cover 17 may be mechanically bonded with the common substrate 13 by a bonding means 18. The bonding means 18 may be at least one of solder, a conductive adhesive or a non-conductive adhesive.

The bonding means 18 may be applied inside the cover 17, as depicted in FIG. 5, or outside the cover 17. The bonding means 18 may be applied continuously around the cover 17. The bonding means 18 may also be applied discontinuously at the cover 17, for example, by one or more individual soldering spots.

The apparatus 10 may further comprise a fluid port 19A, 19B. The fluid port 19A may be provided in the common substrate 13, as depicted in FIG. 5. Additionally or alternatively, a fluid port 19B may be provided in the cover 17, which is indicated by means of dashed lines in FIG. 5.

The fluid port 19A, 19B may provide a fluidic connection between an inside 20 and an outside 21 of the apparatus 10. The cover 17 may serve as a system border for determining an inside 20 and an outside 21 of the apparatus. Accordingly, an inside 20 of the apparatus 10 may be a space at the inside of the cover 17, while an outside 21 of the apparatus 10 may be a space outside the cover 17.

In an example, the device 11 configured to determine a hydrodynamic pressure of the fluid may be a microphone comprising a membrane 22. As can be seen in FIG. 5, the fluid port 19A, 19B may be arranged in the vicinity of the microphone 11 such that sound waves travelling through the fluid port 19A, 19B are directed onto the membrane 22 of the microphone 11.

The apparatus 10 may comprise an external contact 23, such as a contact pad, for example. The external contact 23 may provide for an electrical connection to other electrical components or devices, such as PCBs (Printed Circuit Board) or the like. The external contact 23 may be electrically coupled with the ASIC 14 by means of an electrical conductor 15C.

As can be seen in FIG. 5, the ASIC 14 is arranged within the common substrate 13 such that it is at least partially positioned underneath the sensor 12. Additionally or alternatively, the ASIC 14 may be positioned underneath the device 11 configured to determine a hydrodynamic pressure of the fluid. In an example, the ASIC 14 may be arranged underneath the device 11 and the fluid port 19A may extend through the ASIC 14.

Figure 6:
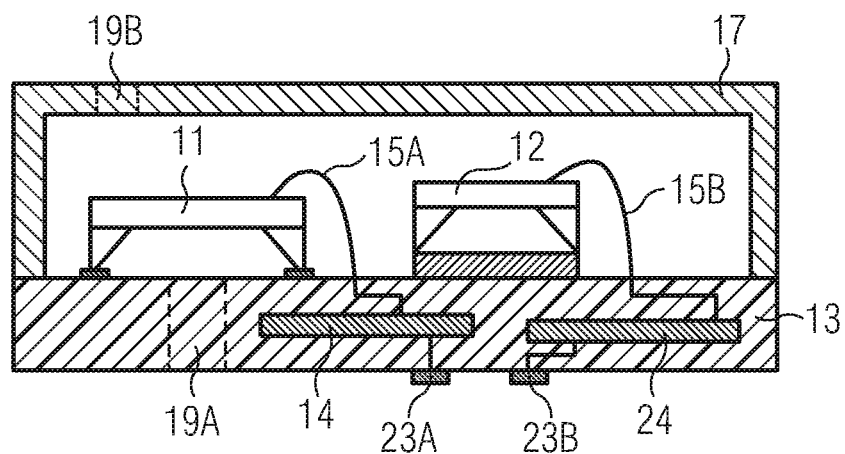
FIG. 6 shows a further schematic side view of an apparatus for determining a characteristic of a fluid according to an example.

FIG. 6 shows a further example of an apparatus 10 according to the present disclosure. The apparatus 10 comprises a first ASIC 14 and a second ASIC 24. The second ASIC 24 may be at least partly embedded in the common substrate 13. In the example shown in FIG. 5, the second ASIC 14 is entirely embedded in the common substrate 13.

The device 11 configured to determine a hydrodynamic pressure of the fluid may be electrically coupled with the first ASIC 14. The sensor 12 may be electrically coupled with the second ASIC 24. However, it may also be possible that the device 11 configured to determine a hydrodynamic pressure of the fluid may be electrically coupled with the second ASIC 24, and that the sensor 12 may be electrically coupled with the first ASIC 14.

At least one of the first and the second ASIC 14, 24 may comprise an external electrical contact 23A, 23B.

Figure 7:
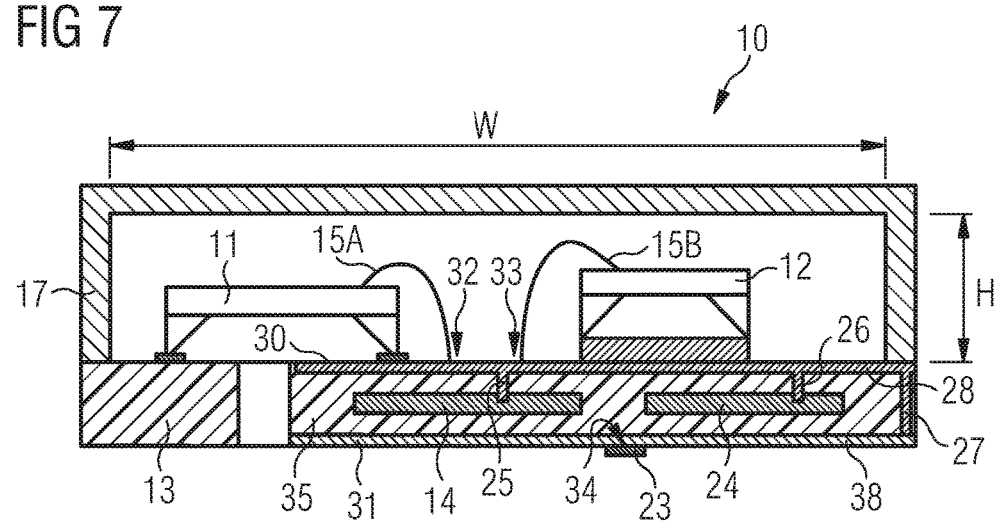
FIG. 7 shows a further schematic side view of an apparatus for determining a characteristic of a fluid according to an example.

FIG. 7 shows a further example of an apparatus 10 in accordance with the present disclosure. The device 11 configured to determine a hydrodynamic pressure of the fluid and the sensor 12 may be electrically coupled with and connected to the ASICs 14, 24 by wire bonds 15A, 15B. Additionally or alternatively, the device 11 and the sensor 12 may be electrically coupled with and connected to the ASICs 14, 24 by a combination of wire bonds 15A, 15B and through filled conductive vias 25, 26, 27.

This arrangement may provide for a connection of the ASICs 14, 24 to the device 11 and the sensor 12, respectively, and to any customer's pads, for example. Additionally, or alternatively, an interface, for example an RDL, may be disposed on to the ASICs 14, 24 which may be used as an interface between the filled vias 25, 26 and contact pads 23 of the ASICs 14, 24.

Output pads 23 located on the bottom of the apparatus 10 may be connected to the ASICs 14, 24 through a metal layer 28 and the filled vias 25, 26, 27 as shown in FIG. 7. The common substrate 13 may be composed of two layer solder masks 30, 31 with openings 32, 33, 34 for the bond pads and the outputs pads 23, two conductive layers 28, 38, through filled vias 25, 26 and an insulating layer 35 that may comprise prepreg material. However, the common substrate 13 may be made of other materials and configurations.

As mentioned above, at least partly embedding the ASIC 14 or the ASICs 14, 24 in the common substrate 13, according to the present disclosure, may result in a reduction in width W of the apparatus 10. Additionally or alternatively, it may also result in a reduction of height H. The width W and the height H are depicted in FIG. 7.

Figure 8:
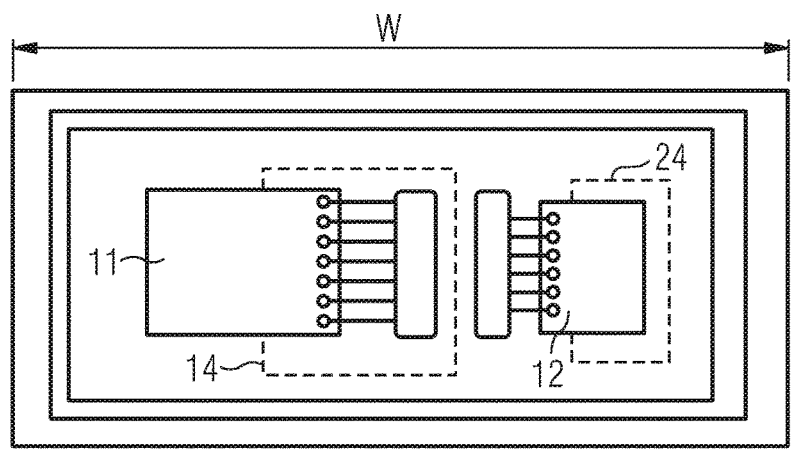
FIG. 8 shows a schematic top view of an apparatus for determining a characteristic of a fluid according to an example.

FIG. 8 shows a top view of the example of FIG. 7 without the cover 17 for the ease of illustration. As can be seen, the device 11 configured to determine a hydrodynamic pressure of the fluid and the sensor 12 are visible as they may be mounted on top of the common substrate 13. The ASICs 14, 24 are shown in dashed lines as they may be entirely embedded in the common substrate 13, and may therefore not be visible.

The positions of the device 11 and the sensor 12 may overlap, at least partially, with the positions of the ASICs 14, 24, as can be seen in the top view of FIG. 8. Accordingly, the width of the apparatus 10 may be reduced.

Figure 9:
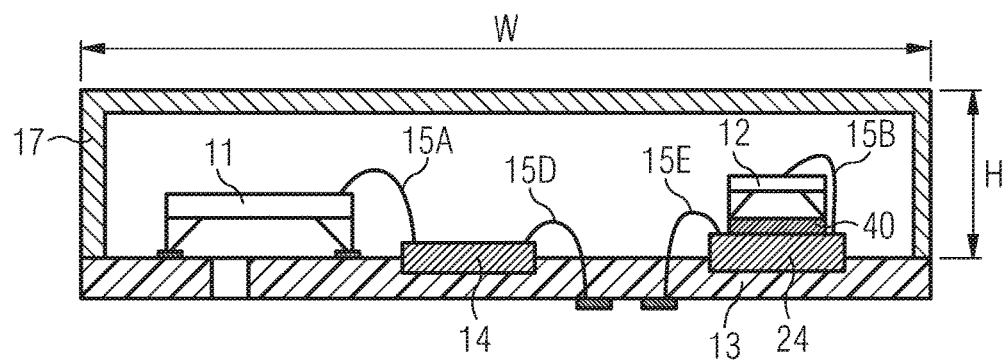
FIG. 9 shows a further schematic side view of an apparatus for determining a characteristic of a fluid according to an example.
Figure 10:
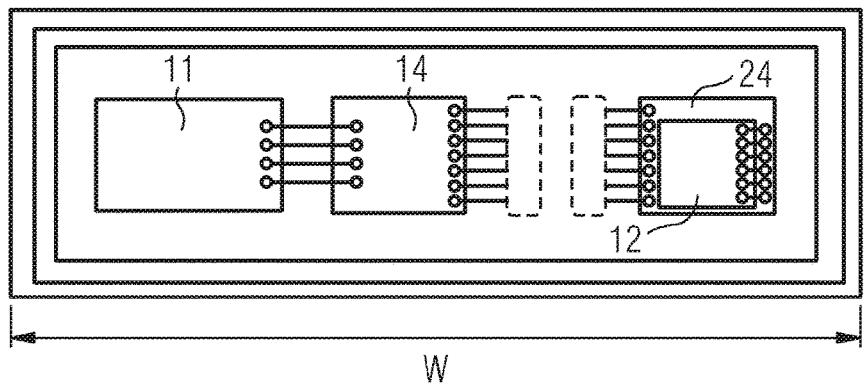
FIG. 10 shows a further schematic top view of an apparatus for determining a characteristic of a fluid according to an example.

For the sake of comparison, FIG. 9 and FIG. 10 show an example of an apparatus 10 with alternative arrangements of the device 11 and the sensor 12 relative to the ASICs 14, 24 such that a wider width W, and a larger height H may result.

As can be seen in FIG. 9, the ASICs 14, 24 are partly embedded in the common substrate 13. Therefore, the first ASIC 14, for example, may be laterally distanced from the device 11. Thus, the width W may be larger as compared to the examples described with reference to FIG. 7 and FIG. 8.

The sensor 12 may be arranged on top of the second ASIC 24, for example. Thus, the height H may be larger as compared to the examples described with reference to FIG. 7 and FIG. 8.

FIG. 10 shows a top view of the example of FIG. 9 without the cover 17 for the ease of illustration. As can be seen, the device 11 configured to determine a hydrodynamic pressure of the fluid and the sensor 12 are visible as they may be mounted on top of the common substrate 13. The ASICs 14, 24 may also be visible as they may at least partly protrude from the top of the common substrate 13. The comparison between the example of FIG. 10 with the previously discussed example of FIG. 8 may reveal that the width W of the example of FIG. 10 may be greater than the width W of the example of FIG. 8.

Figure 11:
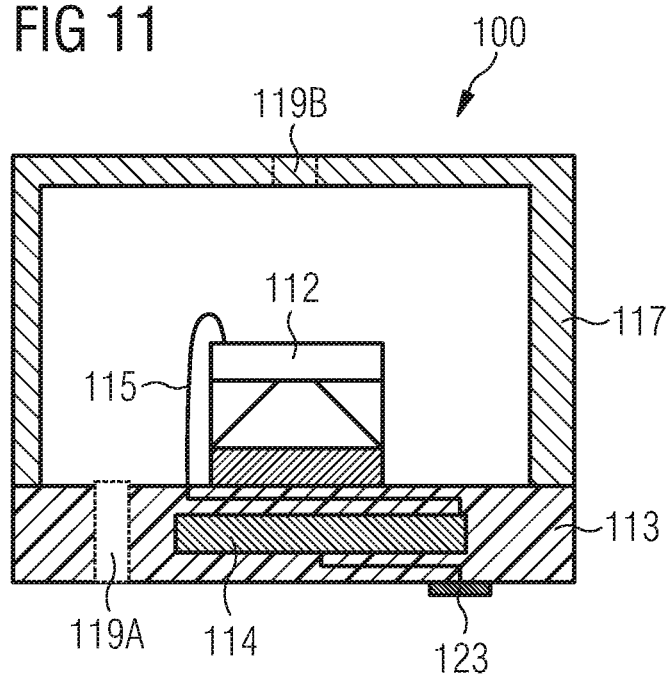
FIG. 11 shows a schematic side view of a device for determining a characteristic of a fluid according to an example.

FIG. 11 shows an example of a device 100 for determining a characteristic of a fluid, in accordance with the present disclosure.

The device 100 may comprise a sensor 112 arranged on a substrate 113. The device 100 may further comprise an ASIC 114 which is electrically coupled with the sensor 112, for example by means of an electrical conductor 115.

The ASIC 114 may be at least partially embedded in the substrate 113. The sensor 112 may be configured to determine a hydrostatic pressure of the fluid. Additionally or alternatively, the sensor 112 may be configured to determine at least one component of the fluid.

The device 100 may comprise a cover 117 which may surround the sensor 112. The cover 117 may be mechanically coupled with the substrate 113. The cover 117 may be mechanically bonded to the substrate 113 by a bonding means, such as solder, a conductive adhesive, or a non-conductive adhesive, for instance.

The device 100 may further comprise a fluid port 119A, 119B. The fluid port 119A may be provided in the substrate, as shown in FIG. 11. Additionally or alternatively, a fluid port 119B may be provided in the cover 117, as shown in dashed lines in FIG. 11. The fluid port 119A, 119B may be provided in the vicinity of the sensor 112.

The sensor 112 may be configured to generate an electrical signal in response to pressure variations of the fluid, wherein the device 100 further comprises a low-pass filter or a bandpass-filter being configured to attenuate electrical signals which are generated in response to pressure variations with a frequency of more than 20 Hz or a frequency of more than 10 Hz.

According to an example, the sensor 112 may be a pressure sensor. The pressure sensor 12 may, for instance, be an air pressure sensor for measuring ambient air pressure. Thus, the sensor 12 may be used for barometric measurements. The sensor 12 may also be configured to measure slow variations of air pressure, which may ensue, for example, due to variations of height, such as during diving, flying or climbing activities.

In an example, the sensor 112 may be a gas sensor configured to determine the concentration of the at least one component of the fluid. Additionally or alternatively, the sensor 112 may be a gas sensor configured to determine the composition of the fluid. Further additionally or alternatively, the sensor 112 may be a gas sensor configured to determine the type of the fluid. Thus, the gas sensor 112 may determine a characteristic of a fluid preferably in its gaseous phase.

A fluid in a gaseous phase may comprise one or more components. As an example, dry ambient air may comprise 78.09% nitrogen, 20.95% oxygen, 0.93% argon, 0.039% carbon dioxide, and small amounts of other gases. Dry ambient air may also comprise a variable amount of water vapor, for example between about 1% at sea level, and about 0.4% over the entire atmosphere.

The gas sensor 112 may be configured to detect or determine at least one component of the fluid, i.e. to identify the respective component, for example, nitrogen, oxygen or the like.

The gas sensor 112 may be configured to determine the concentration of the at least one component of the fluid, i.e. to detect or determine the amount or percentage of the at least one component contained in the fluid.

The gas sensor 112 may be configured to determine the composition of the fluid, i.e. to detect or determine one or more or maybe even all of the components contained in the fluid. The gas sensor 112 may be configured to determine a quantitative composition of the fluid, i.e. to detect or determine the type of a component or components contained in the fluid. The gas sensor 112 may also be configured to determine a qualitative composition of the fluid, i.e. to detect or determine the amount of a component or components contained in the fluid.

The gas sensor 112 may also be configured to detect or determine the type of the fluid, for example to determine that the fluid is dry ambient air.

According to an example, the sensor 112 may be a MEMS, i.e. a Micro-Electro-Mechanical-System. A MEMS may comprise a small form factor which may reduce the form factor or package size of the apparatus of the present disclosure.

Figure 12:
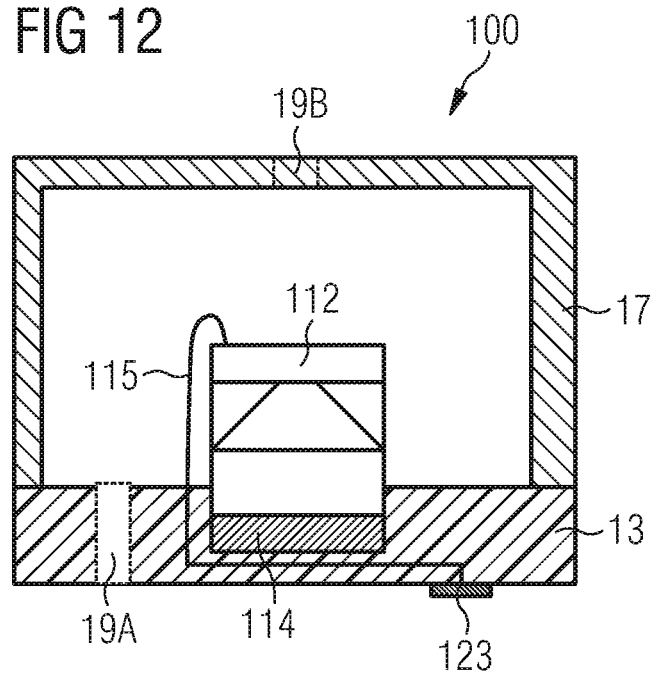
FIG. 12 shows a further schematic side view of a device for determining a characteristic of a fluid according to an example.

FIG. 12 shows a further example of a device 100 according to the present disclosure. The sensor 112 according to this example may be a monolithic sensor 112, wherein the sensor 112 and the ASIC 114 may be monolithically formed. As can be seen, the ASIC 114 is at least partially embedded in the substrate 113.

Figure 13:
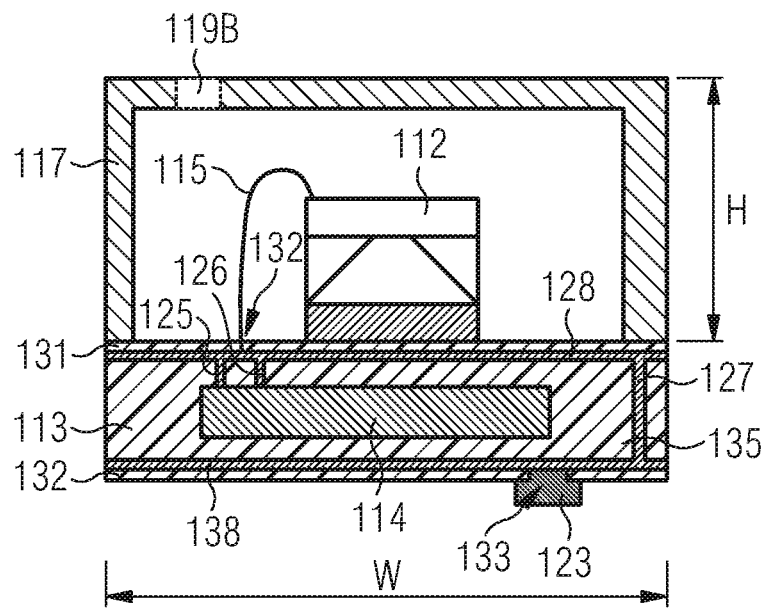
FIG. 13 shows a further schematic side view of a device for determining a characteristic of a fluid according to an example.

FIG. 13 shows a further example of a device 100 according to the present disclosure. The ASIC 114 may be embedded partially or completely under the sensor 112. In an example, the sensor 112 may be directly connected to the ASIC 114 by wire bonds 115. Additionally or alternatively, the sensor 112 may be connected to the ASIC 114 by a combination of wire bonds 115 and through filled conductive vias 125, 126, 127.

This arrangement may provide for a connection between the ASIC 114 and the sensor 112, and optionally to customer's pads. Additionally or alternatively, an interface (e.g. RDL) may be disposed on to the ASIC 114 which may be used to connect the through filled vias 125, 126, 127 and the contact pads of the ASIC 114.

Output pads 123 located on the bottom of the device 100 may be connected to the ASIC 114 through a metal layer 128 and the through filled vias 125, 126, 127.

The substrate 113 may be composed of a solder mask 131, 132 with openings 132, 133 for bond wires 115 and outputs pads 123, two conductive layers 128, 138, filled vias 125, 126, 127 and an insulating layer 135 that may be of prepreg material. However, the substrate 113 may be made of other materials, configurations and dimensions.

Figure 14:
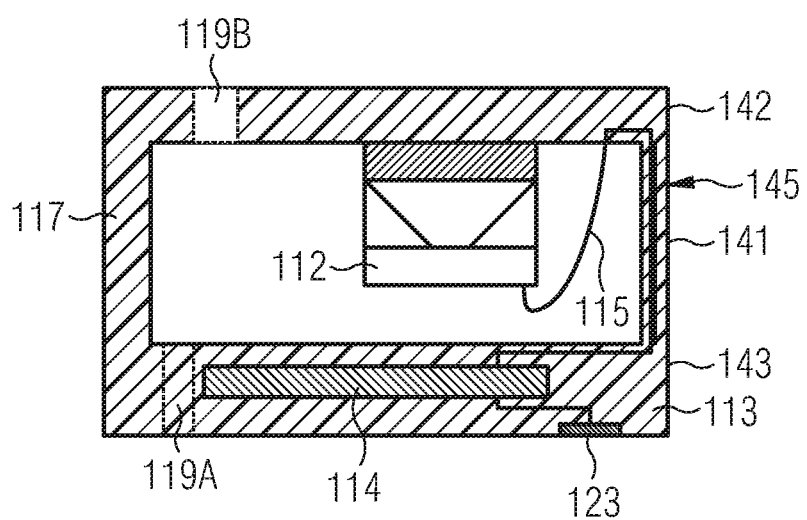
FIG. 14 shows a further schematic side view of a device for determining a characteristic of a fluid according to an example.

FIG. 14 shows a further example of a device 100 according to the present disclosure. In this example, the sensor 112 may be arranged on the cover 117. The cover 117 may be at least partially embedded in the substrate 113. Accordingly, the sensor 112 may be regarded as being arranged on the substrate 113.

The device 100 may further comprise an ASIC 114 that is embedded in the substrate 113.

The sensor 112 may be electrically coupled with the substrate by means of an electric conductor 115. The device 100 may further comprise a through filled via 141 that may connect an upper portion 142 of the device 100 with a lower portion 144 of the device 100. In other words, the device 100 may comprise a filled conductive via 141 that may be applied to a wall portion 145 of the device 100.

FIGS. 15A, 15B, 16A and 16B show further examples of devices 100 according to the present disclosure for purposes of comparison.

Figure 15A:
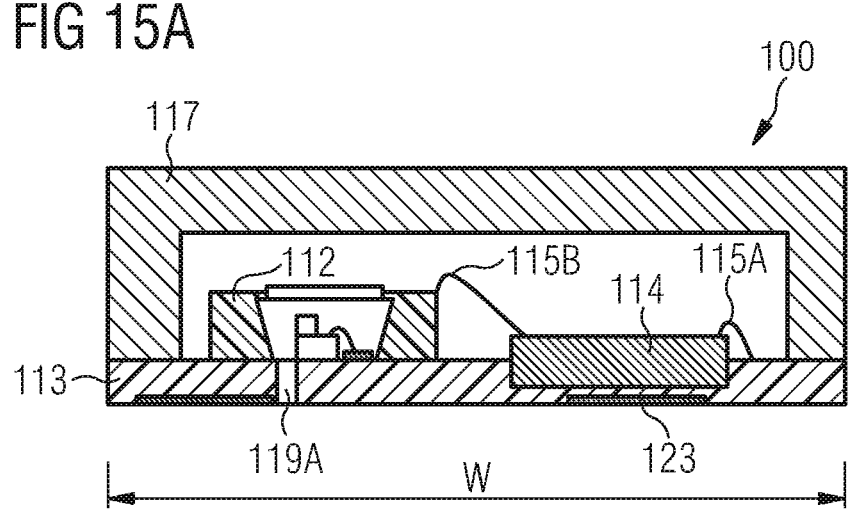
FIG. 15A shows a further schematic side view of a device for determining a characteristic of a fluid according to an example.

FIG. 15A shows a device 100 comprising a sensor 112 which is arranged on a substrate 113. The device 100 further comprises an ASIC 114. The ASIC 114 is at least partially embedded in the substrate 113.

The ASIC 114 is laterally spaced from the sensor 112 by a lateral distance. Thus, the substrate 113 may comprise a certain width W in order to provide enough space to accommodate the sensor 112 and the ASIC 114.

Figure 15B:
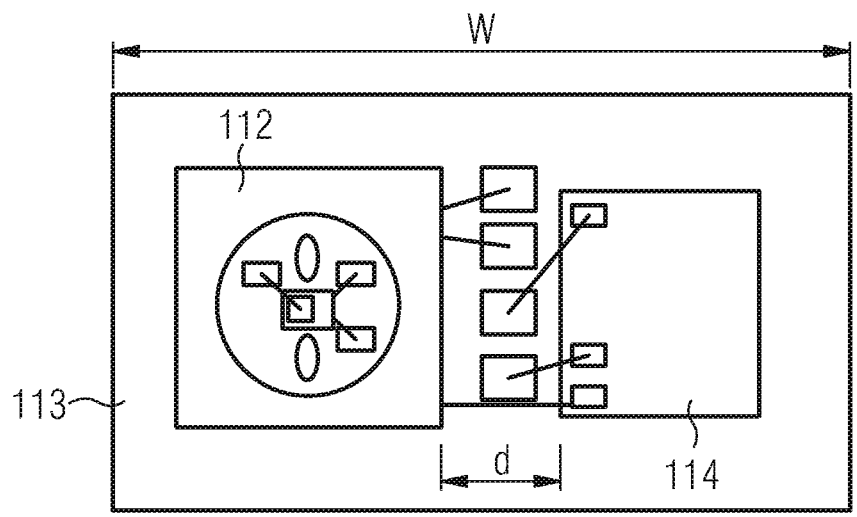
FIG. 15B shows a schematic top view of the device for determining a characteristic of a fluid according to FIG. 15A.

FIG. 15B shows a top view of the device 100. FIG. 15B shows the aforementioned lateral distance d between the sensor 112 and the ASIC 114. Accordingly, the ASIC 114 may be laterally spaced from the sensor 112 in a width direction W by a distance d.

Figure 16A:
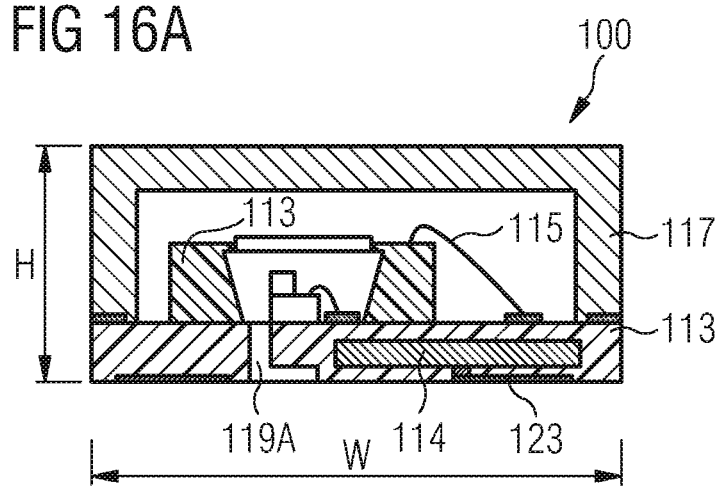
FIG. 16A shows a schematic side view of a device for determining a characteristic of a fluid according to an example.

FIG. 16A shows a device 100 comprising a sensor 112 which is arranged on a substrate 113. The device 100 further comprises an ASIC 114. The ASIC 114 is entirely embedded in the substrate 113.

The ASIC 114 may be arranged underneath the sensor 112 in a height direction H. Additionally or alternatively, the ASIC 114 may be arranged at least partially laterally spaced from the sensor 112 in a width direction W.

Figure 16B:
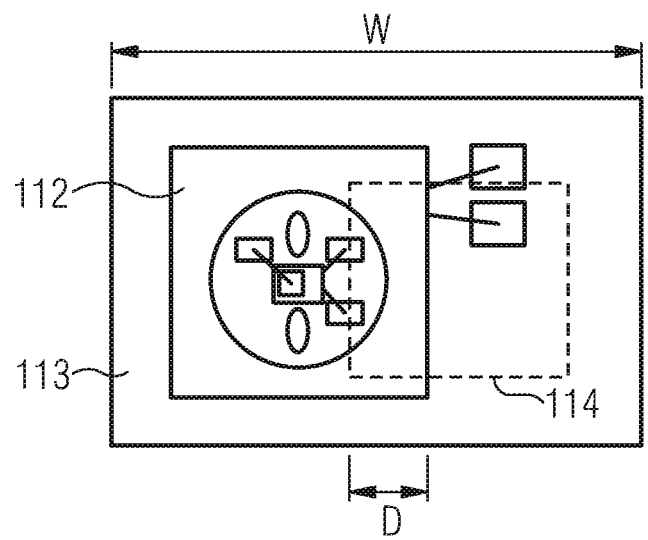
FIG. 16B shows a schematic top view of the device for determining a characteristic of a fluid according to FIG. 16A.

FIG. 16B shows a top view of the device 100. As can be seen, the ASIC 114 may be at least partially laterally spaced from the sensor 112 in a width direction W. The profile of the ASIC 114 and the profile of the sensor 112, when viewed in a top view, may at least partially overlap by a distance D.

According to an example, the ASIC 114 may be completely arranged underneath the sensor 112, both in a height direction H and in a width direction W.

Comparing the device 100 of FIGS. 15A, 15B with the device 100 of FIGS. 16A, 16B, it can be seen that the width W of the device of FIGS. 16A, 16B may be reduced compared to the width W of the device 100 of FIGS. 15A, 15B.

Figure 17:
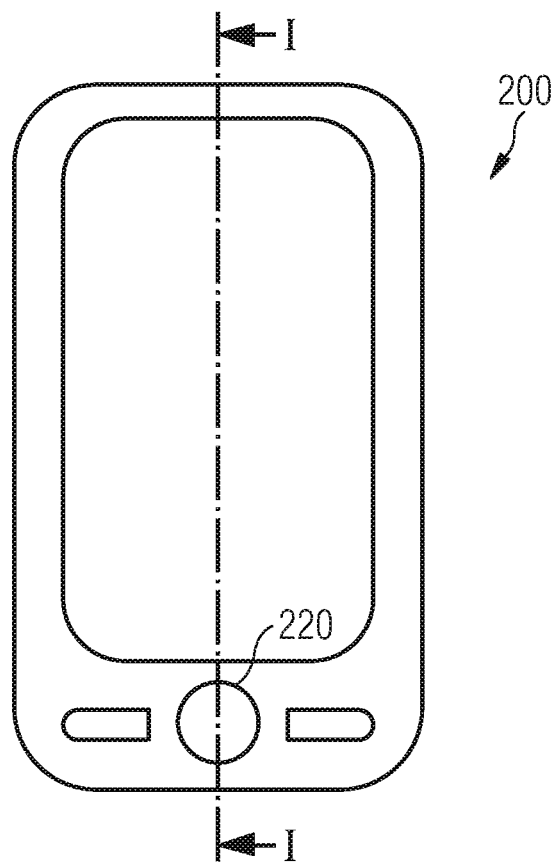
FIG. 17 shows a schematic front view onto a communication device according to an example.
Figure 19:
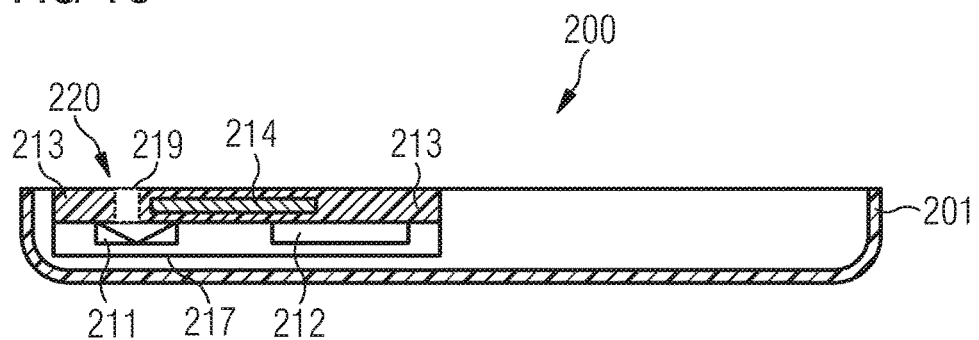
FIG. 19 shows a schematic cross-sectional side view on the device of FIG. 17 along a cross-sectional line I-I in FIG. 17.

FIG. 17 shows an example of a communication device 200 according to an example. The communication device 200 may comprise a microphone opening 220. A microphone may be arranged behind the microphone opening 220. Sound waves may pass through the microphone opening 220. FIG. 19 shows a cross sectional view of the communication device 200 along the cross-section line I-I.

Figure 18:
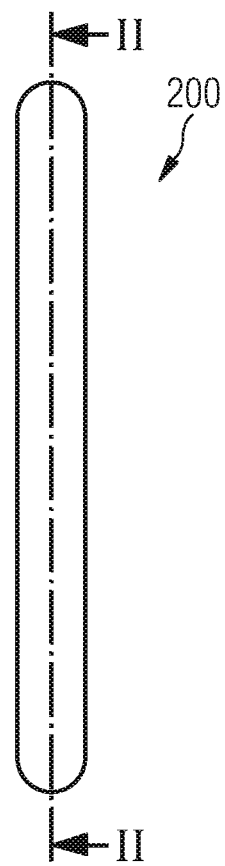
FIG. 18 shows a schematic side view onto the communication device of FIG. 17.

FIG. 18 shows a side view of the communication device 200, and FIG. 19 shows a cross sectional view of the communication device 200 along the cross-section line II-II.

Figure 20:
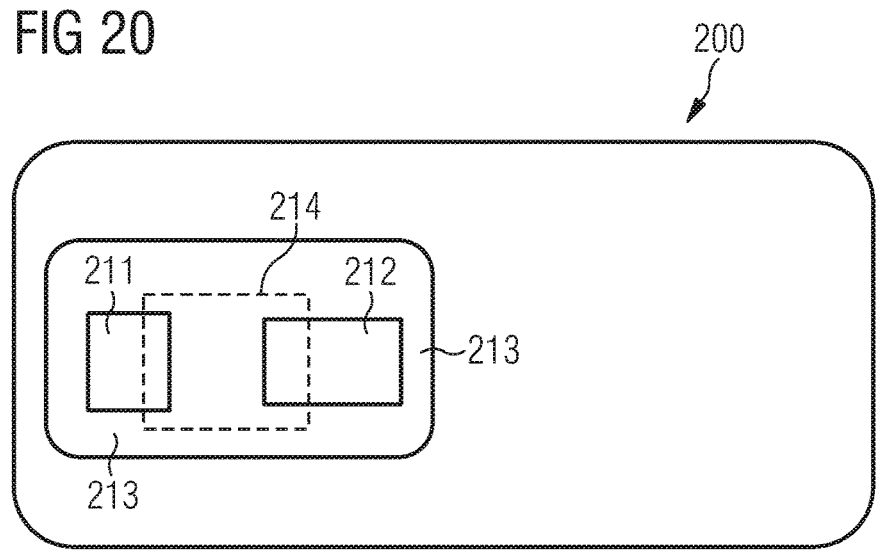
FIG. 20 shows a schematic cross-sectional top view on the device of FIG. 17 along a cross-sectional line II-II in FIG. 18.

Referring to FIGS. 19 and 20, it can be seen that the communication device 200 may comprise a microphone 211 and a sensor 212 to determine a hydrostatic pressure of a fluid or at least one component of the fluid.

The communication device 200 may further comprise a common substrate 213 on which the microphone 211 and the sensor 212 may be commonly arranged.

The communication device 200 may further comprise an ASIC 214 which may be electrically coupled with at least one of the microphone 211 and the sensor 212. The ASIC 214 may be at least partially embedded in the common substrate 213.

The communication device 200 may further comprise a fluid port 219 that provides a fluidic connection between an inside and an outside of the communication device 200.

The microphone 211, the sensor 212, the common substrate 213 and the ASIC 214 being at least partially embedded in the substrate 213 may be arranged inside the communication device 200. The communication device 200 may comprise a housing 201. The microphone 211, the sensor 212, the common substrate 213 and the ASIC 214 being at least partially embedded in the substrate 213 may be arranged inside the housing 201.

The communication device 200 may be a mobile phone, a smartphone, a walkie talkie or the like. The fluid port 219 may be the aforementioned microphone opening 220 provided in the communication device. Additionally or alternatively, the fluid port 219 may be fluidically coupled to the aforementioned microphone opening 220 provided in the communication device.

The microphone 211, the sensor 212, the common substrate 213 and the ASIC 214 being at least partially embedded in the substrate 213 may be substantially the same as previously discussed with reference to FIGS. 1 to 10. In other words, an apparatus 10 according to the present disclosure, and as discussed with reference to FIGS. 1 to 10, may be used in connection with the communication device 200. A microphone which may already be present in the communication device 200 may be used for the present disclosure.

In further examples, the sensor 212, the substrate 213 and the ASIC 214 being at least partially embedded in the substrate 213 may be substantially the same as previously discussed with reference to FIGS. 11 to 116B. In other words, a device 100 according to the present disclosure, and as discussed with reference to FIGS. 11 to 16B, may be used in connection with the communication device 200.

Furthermore, the examples of the present disclosure may be combined as set out below.

In accordance with an example, an apparatus for determining a characteristic of a fluid, the apparatus includes a device configured to determine a hydrodynamic pressure of the fluid; a sensor configured to determine a hydrostatic pressure of the fluid or at least one component of the fluid; a common substrate on which the sensor and the device configured to determine a hydrodynamic pressure of the fluid are arranged; and an ASIC (Application Specific Integrated Circuit) being electrically coupled with at least one of the sensor and the device to determine a hydrodynamic pressure of the fluid. The ASIC is at least partly embedded in the common substrate.

Implementations may include one or more of the following features. The apparatus according to the preceding example where the ASIC is entirely embedded in the common substrate. The apparatus according to one of the preceding examples where the device configured to determine a hydrodynamic pressure of the fluid is at least one of a mechanical device, an electrical device or an electromechanical device. The apparatus according to one of the preceding examples, where the device configured to determine a hydrodynamic pressure of the fluid is a microphone. The apparatus according to one of the preceding examples, where the sensor is a pressure sensor. The apparatus according to one of the preceding examples, where the sensor is configured to generate electrical signals in response to pressure variations of the fluid, where the apparatus further comprises a low-pass filter or a bandpass-filter configured to attenuate electrical signals from the sensor which electrical signals are generated in response to pressure variations with a frequency of more than 20 Hz or with a frequency of more than 10 Hz. The apparatus according to one of the preceding examples, where the sensor is a gas sensor configured to determine the concentration of the at least one component of the fluid or to determine at least one of the composition and the type of the fluid. The apparatus according to one of the preceding examples, where at least one of the sensor and the device configured to determine a hydrodynamic pressure of the fluid is a MEMS (Micro-Electro-Mechanical-System). The apparatus according to one of the preceding examples, where the ASIC is electrically coupled with the sensor and with the device configured to determine a hydrodynamic pressure of the fluid.

Implementations may further include one or more of the following features. The apparatus according to one of the preceding examples, further including a second ASIC that is at least partly embedded in the common substrate, wherein the device configured to determine a hydrodynamic pressure of the fluid is electrically coupled with the first ASIC and the sensor is electrically coupled with the second ASIC. The apparatus according to one of the preceding examples, further including a cover that is mechanically coupled with the common substrate and which surrounds the sensor and the device configured to determine a hydrodynamic pressure of the fluid. The apparatus according to a previous example where the cover is mechanically bonded with the common substrate by a bonding means that comprises at least one of solder, a conductive adhesive or a non-conductive adhesive. The apparatus according a previous example, further including a fluid port that is provided in at least one of the cover and the common substrate, which fluid port provides a fluidic connection between an inside and an outside of the apparatus for determining a characteristic of a fluid. The apparatus according to a previous example, where the device configured to determine a hydrodynamic pressure of the fluid is a microphone and wherein the fluid port is arranged in the vicinity of the microphone such that sound waves travelling through the fluid port are directed onto a membrane of the microphone.

In accordance with a further example, A device for determining a characteristic of a fluid including a sensor being arranged on a substrate; an ASIC being electrically coupled with the sensor and being at least partially embedded in the substrate, where the sensor is configured to determine a hydrostatic pressure of the fluid or at least one component of the fluid.

Implementations may further include one or more of the following features. The device for determining a characteristic of a fluid where the sensor is configured to generate an electrical signal in response to pressure variations of the fluid, and where the device further comprises a low-pass filter or a bandpass-filter being configured to attenuate electrical signals which are generated in response to pressure variations with a frequency of more than 20 Hz or a frequency of more than 10 Hz. The device for determining a characteristic of a fluid according to a previous example where the sensor is a pressure sensor. The device for determining a characteristic of a fluid according to a previous example where the sensor is a gas sensor configured to determine the concentration of the at least one component of the fluid or to determine at least one of the composition and the type of the fluid. The device for determining a characteristic of a fluid according a previous example, further comprising a cover that is mechanically coupled with the substrate and which surrounds the sensor, and where the cover is mechanically bonded with the substrate by a bonding means that comprises at least one of solder, a conductive adhesive or a non-conductive adhesive.

In accordance with a further example, a communication device includes a microphone; a sensor to determine a hydrostatic pressure of a fluid or at least one component of the fluid; a common substrate on which the microphone and the sensor are arranged; an ASIC (Application Specific Integrated Circuit) being electrically coupled with at least one of the microphone or the sensor; and a fluid port that provides a fluidic connection between an inside and an outside of the communication device; where the ASIC is at least partly embedded in the common substrate. Implementations may include a communication device that includes an apparatus according to one of the previous examples.

The apparatuses and devices of the present disclosure may provide for some advantages. For example, with the continuous demand from the market to offer a reduced package size it may become relevant to find spaces where common concepts were not thought of from the beginning. In this disclosure it is proposed a way of reducing the footprint of an apparatus or device, such as a pressure package, for example. According to examples, this may be achieved by embedding an ASIC and/or other integrated circuit to a substrate, as described above. Today, markets such as the mobile industry may wish that these types of packages have a smaller package size.

For example, a device as described above, such as a pressure MEMS or the like, may be attached to the top of an ASIC by means of silicon glue. The ASIC may be placed on to the substrate's surface and these two components may be used to sense and analyze an atmospheric pressure, for example, that may enter an open port. The ASIC may be used for processing signals from the MEMS and once processed, the signals may be sent to external pads that may be connected to a customer's PCB, for example. In order for these internal components to be protected from undesirable external conditions, a cover, such as a stainless steel lid for example, may be applied above which may be glued or soldered to the substrate.

Today, due to design rules, it may be necessary to leave distances between components such as lid, MEMS, ASIC, substrate and bond wires and as expected the package size may become bigger for every included component.

As mentioned above, the apparatuses and devices according to the present disclosure may enable a reduction in package size. According to some examples, a space in the substrate may be used for embedding an ASIC while maintaining a sensor's performance.

According to some examples, a customer may have a thinner package and subsequently resulting in thinner products. Today, mobile phone manufacturers, for instance, may be placing a pressure sensor near the SIM slot. However, studies may have indicated that the SIM card will no longer be used on a phone and therefore a different location may have to be found for a sensor, such as a pressure sensor for example. According to some examples which may comprise a microphone and a pressure sensor, for instance, this may eliminate the need to look for a new position in the customer's PCB.

In this regard, the market may demand to offer bundle solutions in a package, wherein it may become possible to include a microphone and a pressure MEMS, for instance, in one package since both of them may be compatible. Today, having two MEMS devices bundled together will consequently make a package very big which neither brings an advantage to the microphone performance nor is it relevant for the consumer market as they prefer to have a small package.

However, having a sensor and a device configured to determine a hydrodynamic pressure of a fluid bundled together, as described in some of the examples above, may reduce the package size.

The present disclosure may enable a reduction in the overall size of a package in which the ASICs of sensors and devices as described above, such as MEMS for example, may be embedded in the substrate. With reference to the previously described Figures above, and in accordance with one or more examples according to the present disclosure, using an unused space in a substrate may provide for embedding one or more ASICs resulting in a reduction of the size of the package. With a configuration according to the present disclosure, the package may potentially be reduced by 50% compared to conventional systems.

Users or customers may have the advantage of using one package that contains two types of sensors, e.g. a sensor for determining a hydrostatic pressure and a sensor for determining a hydrodynamic pressure, for example, optimizing their production cycle time and reducing the space on their PCB. Furthermore, one package may use the same opening port for both sensors.

One or more examples of the present disclosure may provide for having two distinct devices, such as MEMS for example, in one reduced package size.

Although some aspects may have been described in the context of an apparatus or device, these aspects may also represent a description of a corresponding method, where a block or device may correspond to a method step or a feature of a method step. Analogously, aspects described in the context of a method step may also represent a description of a corresponding block or item or feature of a corresponding apparatus or device.

Depending on certain implementation requirements, one or more embodiments of the present disclosure may be implemented in hardware or in software. The implementation may be performed using a digital storage medium, for example a floppy disk, a DVD, a CD, a ROM, a PROM, an EPROM, an EEPROM or a FLASH memory, having electronically readable control signals stored thereon, which cooperate (or are capable of cooperating) with a programmable computer system such that the respective method is performed.

One or more embodiments of the present disclosure may comprise a data carrier having electronically readable control signals, which may be capable of cooperating with a programmable computer system, such that one of the methods described herein is performed.

Generally, embodiments of the present disclosure may be implemented as a computer program product with a program code, the program code being operative for performing one of the methods when the computer program product runs on a computer. The program code may for example be stored on a machine readable carrier.

Other embodiments may comprise the computer program for performing one of the methods described herein, stored on a machine readable carrier.

In other words, one or more of the embodiments of a method according to the present disclosure may therefore be a computer program having a program code for performing one of the methods described herein, when the computer program runs on a computer.

One or more further embodiments of a method according to the present disclosure may be a data carrier (or a digital storage medium, or a computer-readable medium) comprising, recorded thereon, the computer program for performing one of the methods described herein.

One or more further embodiments of a method according to the present disclosure may be a data stream or a sequence of signals representing the computer program for performing one of the methods described herein. The data stream or the sequence of signals may for example be configured to be transferred via a data communication connection, for example via the Internet.

One or more further embodiments may comprise a processing means, for example a computer, or a programmable logic device, configured to or adapted to perform one of the methods described herein.

One or more further embodiments may comprise a computer having installed thereon the computer program for performing one of the methods described herein.

In some embodiments, a programmable logic device (for example a field programmable gate array) may be used to perform some or all of the functionalities of the methods described herein. In one or more embodiments, a field programmable gate array may cooperate with a microprocessor in order to perform one of the methods described herein. Generally, the methods may be performed by any hardware apparatus.

The above described embodiments are merely illustrative for the principles of the present disclosure. It is understood that modifications and variations of the arrangements and the details described herein will be apparent to others skilled in the art. It is the intent, therefore, to be limited only by the scope of the impending patent claims and not by the specific details presented by way of description and explanation of the embodiments herein.

What is claimed is:

1. An apparatus for determining a characteristic of a fluid, the apparatus comprising:
   a device configured to determine a hydrodynamic pressure of the fluid;
   a sensor configured to determine a hydrostatic pressure of the fluid or at least one component of the fluid;
   a common substrate on which the sensor and the device configured to determine the hydrodynamic pressure of the fluid are arranged; and
   a first ASIC (Application Specific Integrated Circuit) being electrically coupled with at least one of the sensor and the device to determine the hydrodynamic pressure of the fluid, wherein the first ASIC is at least partly embedded in the common substrate.

2. The apparatus according to claim 1, wherein the first ASIC is entirely embedded in the common substrate.

3. The apparatus according to claim 1, wherein the device configured to determine the hydrodynamic pressure of the fluid is at least one of a mechanical device, an electrical device or an electromechanical device.

4. The apparatus according to claim 1, wherein the device configured to determine the hydrodynamic pressure of the fluid is a microphone.

5. The apparatus according to claim 1, wherein the sensor is a pressure sensor.

6. The apparatus according to claim 1, wherein the sensor is configured to generate electrical signals in response to pressure variations of the fluid, wherein the apparatus further comprises a low-pass filter or a bandpass-filter configured to attenuate electrical signals from the sensor which electrical signals are generated in response to pressure variations with a frequency of more than 20 Hz or with a frequency of more than 10 Hz.

7. The apparatus according to claim 1, wherein the sensor is a gas sensor configured to determine a concentration of the at least one component of the fluid or to determine at least one of a composition and a type of the fluid.

8. The apparatus according to claim 1, wherein at least one of the sensor and the device configured to determine the hydrodynamic pressure of the fluid is a MEMS (Micro-Electro-Mechanical-System).

9. The apparatus according to claim 1, wherein the first ASIC is electrically coupled with the sensor and with the device configured to determine the hydrodynamic pressure of the fluid.

10. The apparatus according to claim 1 further comprising a second ASIC that is at least partly embedded in the common substrate, wherein the device configured to determine the hydrodynamic pressure of the fluid is electrically coupled with the first ASIC and the sensor is electrically coupled with the second ASIC.

11. The apparatus according to claim 1 further comprising a cover that is mechanically coupled with the common substrate and which surrounds the sensor and the device configured to determine the hydrodynamic pressure of the fluid.

12. The apparatus according to claim 11, wherein the cover is mechanically bonded with the common substrate by a bonding means that comprises at least one of solder, a conductive adhesive or a non-conductive adhesive.

13. The apparatus according to claim 11, further comprising a fluid port that is provided in at least one of the cover and the common substrate, which fluid port provides a fluidic connection between an inside and an outside of the apparatus for determining the characteristic of a fluid.

14. The apparatus according to claim 13, wherein the device configured to determine the hydrodynamic pressure of the fluid is a microphone and wherein the fluid port is arranged in the vicinity of the microphone such that sound waves travelling through the fluid port are directed onto a membrane of the microphone.

15. A method of making an apparatus for determining a characteristic of a fluid, the method comprising:
   providing a device configured to determine a hydrodynamic pressure of the fluid;
   providing a sensor configured to determine a hydrostatic pressure of the fluid or at least one component of the fluid;
   providing a common substrate;
   arranging the sensor and the device configured to determine the hydrodynamic pressure of the fluid on the common substrate;
   electrically coupling a first ASIC (Application Specific Integrated Circuit) with at least one of the sensor and the device to determine the hydrodynamic pressure of the fluid; and
   at least partially embedding the first ASIC in the common substrate.

16. The method of claim 15, wherein at least partially embedding the first ASIC in the common substrate comprises entirely embedding the first ASIC in the common substrate.

17. The method of claim 15, further comprising mechanically coupling a cover with the common substrate, wherein the cover and the common substrate surrounds the sensor and the device configured to determine the hydrodynamic pressure of the fluid.

18. The method according to claim 17, wherein mechanically coupling the cover comprises mechanically bonding the cover to the common substrate using at least one of solder, a conductive adhesive or a non-conductive adhesive.

19. A method of operating an apparatus for determining a characteristic of a fluid comprising a device, a sensor, a common substrate on which the sensor and the device are arranged, a first ASIC (Application Specific Integrated Circuit) being electrically coupled with at least one of the sensor and the device, wherein the first ASIC is at least partly embedded in the common substrate, the method comprising:
  determining, by the device, a hydrodynamic pressure of the fluid; and
  determining, by the sensor, a hydrostatic pressure of the fluid or at least one component of the fluid.

20. The method of claim 19, further comprising generating, by the sensor, electrical signals in response to pressure variations of the fluid.

* * * * *